(12) United States Patent
Inui

(10) Patent No.: US 7,923,546 B2
(45) Date of Patent: Apr. 12, 2011

(54) BASE SEQUENCE FOR CONTROL PROBE AND METHOD OF DESIGNING THE SAME

(75) Inventor: Mimune Inui, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1463 days.

(21) Appl. No.: 11/350,947

(22) Filed: Feb. 10, 2006

(65) Prior Publication Data

US 2006/0269933 A1 Nov. 30, 2006

(30) Foreign Application Priority Data

Feb. 14, 2005 (JP) ................................. 2005-036545

(51) Int. Cl.
C07H 21/04 (2006.01)
C12Q 1/68 (2006.01)
C07K 2/00 (2006.01)

(52) U.S. Cl. .......... 536/24.1; 435/6; 536/23.1; 530/300; 530/350

(58) Field of Classification Search ........................ None
See application file for complete search history.

(56) References Cited

U.S. PATENT DOCUMENTS

| 5,556,749 A | 9/1996 | Mitsuhashi et al. ............... 435/6 |
| 7,192,745 B2 | 3/2007 | Jaeger .......................... 435/91.2 |

FOREIGN PATENT DOCUMENTS

| EP | 1 452 598 | 9/2004 |
| JP | 2002-335981 | 11/2002 |
| WO | 97/10365 | 3/1997 |
| WO | 2005/001123 | 1/2005 |

OTHER PUBLICATIONS

Giel-Pietraszuk et al., Journal of Protein Chemistry, vol. 22, No. 2, Feb. 2003.*
Leparc et al., Nucleic Acids Research, vol. 37, No. 3, Dec. 2008.*
Paul Hardenbol, et al., "Identification of preferred hTBP DNA binding sites by the combinatorial method REPSA", Nucleic Acids Research, vol. 25, No. 16, 1997, pp. 3339-3344.
Wuju Li, et al., "MProbe: computer aided probe design for oligonucleotide microarrays", Applied Bioinformatics, Open Mind Journals, vol. 1, No. 3, 2002, pp. 163-166.
Russell Roslin, "Designing microarry oligonucleotide probes", Briefings in Bioinformatics, vol. 4, No. 4, Dec. 2003, pp. 361-367.

* cited by examiner

Primary Examiner — Shubo (Joe) Zhou
(74) Attorney, Agent, or Firm — Fitzpatrick, Cella, Harper & Scinto

(57) ABSTRACT

There are provided a sequence for a control probe having a sequence rarely forming a secondary structure and rarely hybridizing with an undesired target and a method of designing thereof. There is further provided a probe carrier employing a control probe designed by the designing method. To provide these, a palindromic sequence is selected based on a sequence of which frequency is low in a database for a predetermined base sequence and used as the sequence of the control probe.

3 Claims, 5 Drawing Sheets

BASE SEQUENCE FOR CONTROL PROBE AND METHOD OF DESIGNING THE SAME

BACKGROUND OF THE INVENTION

1. Field of the Invention

The present invention relates to a technique for designing a suitable sequence for a control probe which is used in determining a dynamic range of a probe array, having a solid-phase carrier with probes immobilized thereon, such as a DNA microarray.

2. Related Background Art

In detecting a target nucleic acid, a control nucleic acid (control probe) is often used in order to minimize the influence caused by detection errors (see Japanese Patent Application Laid-Open No. 2002-335981). The control probe used in a DNA microarray for use in detecting bacteria is generally designed based on a sequence derived from the bacteria present in the natural world as a reference. The control probe is used in a DNA microarray or the like to, know its dynamic range. To explain more specifically, if a complementary sequence (single stranded DNA sequence) to that of a control probe is present in a sample containing a target, the complementary sequence (single stranded DNA sequence) can be detected by the control probe immobilized onto a DNA microarray based on a hybridization reaction between the sample and the array. In this manner, the dynamic range of the array can be identified.

SUMMARY OF THE INVENTION

When a single stranded DNA used as a control probe has sequences complementary to each other in its own sequence, a higher-order structure, so-called a secondary structure, may be sometimes formed by hydrogen bonds of itself. When a control probe has such a secondary structure formed therein, it becomes difficult for the control probe to hybridize with a target single stranded DNA, failing to sufficiently work as a control probe. On the other hand, when a control probe is designed to have a sequence frequently present in the natural world, it will bind to an undesired target, providing undesirable results. Therefore, as the sequence of a control probe that functions properly, it is desired to obtain a unique sequence rarely found in the natural world, and rarely forming a secondary structure and hybridizing with an undesired target.

The present invention has been attained in view of the aforementioned circumstances. An object of the present invention is to provide a control probe sequence which rarely forms a secondary structure and hybridizes with an undesired target and a designing method for the control probe sequence, and further provide a probe carrier using the control probe created by the designing method.

More specifically, a control probe according to the present invention comprises one base sequence heading from the center of the sequence of the probe toward an end thereof and another base sequence heading from the center toward the other end thereof, both of the base sequences being uncomplementary to each other.

The base sequence heading toward one end has a base length of which average number of frequency is lowest (Na is not zero) in a database and of which frequency is lowest for that base length.

According to one aspect of the present invention, a control probe comprises a palindromic base sequence.

The method of designing a control probe sequence according to the present invention is characterized by comprising the steps of:

selecting the lowest frequent sequence, of which frequency is lowest, from among the sequences of genes stored in a database; and selecting a sequence containing the lowest frequent sequence as a control probe sequence, wherein the sequence comprises a base sequence heading from the center of the probe sequence toward one end thereof, and another base sequence heading from the center toward the other end thereof, both of the base sequences being uncomplementary to each other, thereby determining the sequence of the control probe.

Further, one aspect of a method designing for a control probe sequence according to the present invention comprises the steps of:

obtaining an average number of frequency (N) of each of the base sequences having 3 base length or more in the sequences of genes stored in a database;

determining a base length of which average number of frequency (Na) is lowest (Na is not 0);

selecting the lowest frequent sequence of which frequency is lowest, from among the sequences having the base length of which average number of frequency (Na) is lowest; and determining the sequence of the control probe by selecting a palindromic sequence containing the lowest frequent sequence as a control probe.

A probe carrier according to the present invention is characteristic in that a control probe having the sequence designed by the aforementioned method and probes for detecting a target sequence contained in a specimen are immobilized on a solid phase.

A nucleic acid detection kit according to the present invention comprises the aforementioned probe carrier and an artificial nucleic acid having a complementary sequence to that of the control probe.

According to the present invention, it is possible to design a control probe rarely forming a secondary structure and binding to an undesired target, and suitably used in confirming a dynamic range of a probe carrier.

Since the control probe according to the present invention is designed based on a sequence present in the natural world, it is considered as being more stable than a sequence artificially constructed.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 illustrates a probe sequence (SEQ ID No. 15) easily forming a secondary structure;

FIG. 2 illustrates a structure of the probe sequence of FIG. 1, folded in half at the center;

FIG. 3 illustrates a palindromic probe sequence (SEQ ID No. 16) which rarely forms a secondary structure;

FIG. 4 illustrates a structure of the probe sequence of FIG. 3, folded in half at the center;

DETAILED DESCRIPTION OF THE PREFERRED EMBODIMENTS

Figure 5:
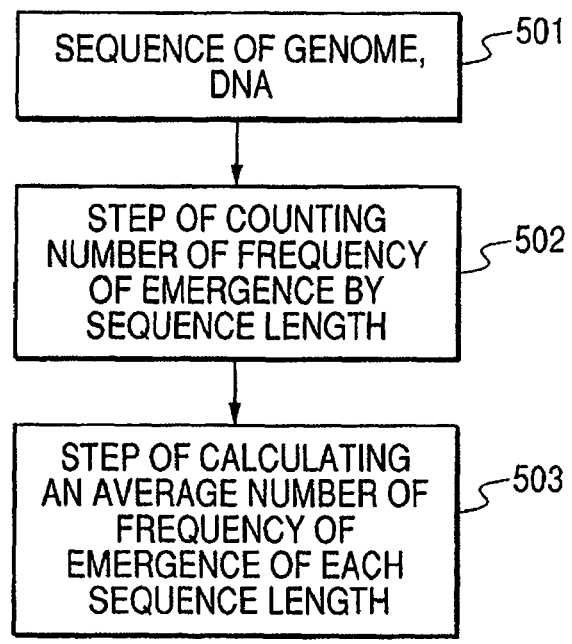
FIG. 5 illustrates a flowchart for calculating an emergence frequency of a sequence.

Preferred embodiments of the present invention will now be described in detail in accordance with the accompanying drawings.

A control probe according to the present invention has a base sequence heading from the center of sequence of the probe toward one end thereof and a base sequence heading from the center toward the other end thereof, both being uncomplementary to each other. As a preferably embodiment, a control probe has a palindromic base sequence containing the base sequence serving as a control probe. As the palindromic base sequence, mention may be specifically made of the sequence represented by SEQ. ID No. 1, in which CGTACGATC has function as a control probe, a sequence "cgtacgatcgat" is arranged on the 5' side of G located at the 13th position from the 5' end, whereas a sequence "tagctagcatgc" is arranged on the 3' side of G. When the sequence "tagctagcatgc" on the 3' side is rearranged one by one from the 3' terminal toward the 5' terminal, the rearranged sequence coincides with the sequence "cgtacgatcgat" of the 5' side. Likewise, a palindromic structure is formed. In the present invention, the palindromic structure is defined as a sequence structure, which is identical if a base sequence is read from the 3' side to the 5' side and from the 5' side to the 3' side. By virtue of the palindromic structure, the aforementioned control probe itself rarely forms a secondary structure.

The term "the center of sequence" used herein refers to a base positioned in the middle, when the sequence consists of odd numbered bases. For example, when a sequence consists of 21 bases, the 11th base is the center.

When a sequence consists of even numbered bases, there is no base present just in the middle of the sequence. In this case, either one of two bases present approximately in the middle may be selected.

A method of designing a control probe according to the present invention has the steps of selecting a lowest frequent sequence, of which frequency is lowest, from the sequences of a gene stored in a database; and selecting a sequence containing the lowest frequent sequence as a control probe, a base sequence heading from the center of the probe sequence toward one end thereof, and an base sequence heading from the center toward the other end thereof, both being uncomplementary to each other, thereby determining the sequence of the control probe.

Preferably, a method of designing a control probe according to the present invention is carried out in accordance with the following steps (A) to (D):

(A) obtaining an average number of frequency (N) of each of the base sequences having 3 base length or more in the gene sequences stored in a database;

(B) determining a base length of which average number of frequency (Na) is lowest (Na is not 0);

(C) selecting the lowest frequent sequence of which frequency is lowest out of the sequences having the base length of which average number of frequency (Na) is lowest; and (D) determining the sequence of the control probe by selecting a palindromic sequence containing the lowest frequent sequence as a control probe.

As the genomic base sequence database, for example, the NCBI UniGene may be mentioned. The gene sequences stored in the database are advantageously used since the number of frequency of the sequence can be counted by a computer.

First, an average number of frequency of each base length of the sequences having 3 to 12 base lengths present in gene sequences of interest is calculated. For example, in the case of 3 base-length sequences present in DNA, an average number of frequency can be obtained as follows. First, the number of frequency of each of the 3 base-length sequences represented by, 5'-XYZ-3', (where X, Y, Z are each independently selected from A, T, C, G) is obtained. Then, the frequency of each of these sequences is divided by the total number of possible sequences ($4^3$) based on the mathematical combination. Note that it is effective in calculating frequency of a predetermined base-length sequence in accordance with the method described in Examples (described later).

Furthermore, an average number of frequency is obtained with respect to the sequences of not less than 4 bases in the same manner as mentioned. A base length of which average number of frequency is lowest is determined from the obtained results. The base length (L) of which average number of frequency is lowest (not 0) means that the average number of frequency of the base length which is longer by one base than L (that is, L+1) comes to zero. Of the sequences having the lowest average base length thus obtained in this manner, a sequence of which frequency is lowest (not 0) is specified. Then, a control probe containing the sequence having the lowest emergence frequency is constructed by arranging a base sequence so as to head from the center of the probe sequence to one end, and a base sequence so as to head from the center to the other end, both being uncomplementary to each other.

Specifically, a palindromic structure is the most preferable as the structure of a control probe since it is easily constructed. However, a control probe may be designed by selecting sequences with uncomplementary bases sequentially.

The control probe constructed in this manner would not form a secondary structure via a hydrogen bond(s) even if folded at the center in half (that is, the length of the folded sequences in contact with each other is the longest). For example, when a single stranded DNA (as shown in FIG. 1) containing complementary sequences in its own sequence is folded into two (as shown in FIG. 2), it forms a secondary structure and its binding force is strong. In contrast, when a single stranded DNA (as shown in FIG. 3) having a palindromic structure is even folded into two (as shown in FIG. 4), the identical bases face each other, with the result that no hydrogen bonding takes place. In general, the longer the length of the folded sequences in contact with each other, the stronger the binding force of hydrogen bonding. For this reason, a single stranded DNA having a palindromic structure effectively works to prevent formation of a secondary structure even when a single stranded DNA is folded in two at the center, and the length of the two folded sequences in contact with each other is the longest).

Note that as shown in Examples (described later), when the base sequences of all the genes contained in the NCBI UniGene database are checked in accordance with the aforementioned procedure, the base length of which average number of frequency is lowest is 9. Of the 9 base sequences, the specific sequence having the lowest frequency is "CGTACGATC". It is the sequence represented by SEQ. ID No. 1 that has a palindromic sequence constructed by using this sequence. The sequence of SEQ. ID No. 1 is effective in preventing a control probe from hybridizing with an undesired target.

EXAMPLES

The present invention will be explained with reference to Examples below.
(Calculation of the Number of Frequency of Emergence and Analysis)

FIG. 5 shows a flowchart for computationally obtaining the number of frequency of emergence. Taking the case where a 4-base sequence occurs in the sequence of ATCGATCG, as an example, the explanation will be made.

In a first step, all possible combinations of a 4 base genomic sequence, XYZW (X to W each independently represent any one of A, T, C, G) are expressed by replacing A, T, C, G with numeric characters. The sequences of (0, 0, 0, 0) to (3, 3, 3, 3) are cleared back to zero (in this Example, A, T, C, G should be replaced with different numeric characters selected from the group of 0 to 3, respectively). Then, in the genomic sequence, ATCGATCG, which is used to calculate the number of frequency of emergence, a particular numeric character selected from 0 to 4 is assigned to each base, therefore the sequence ATCGATCG is expressed as "01230123". In the next step, a series of 4 numeric characters is taken from the front-end of the numeric sequence thus replaced, and then 1 is added to the sequence (0, 1, 2, 3). This 1 means that a genomic sequence ATCG, that is, the numeric sequence (0, 1, 2, 3), occurs once. Then, the 4-digit numeric sequence frame is shifted by one digit rightward from the front end. To the numeric sequence (1, 2, 3, 0) of the next frame is added 1. The same procedures is repeated five times in total until the frame shift operation reaches the tail end of the numeric sequence. In this manner, the total number of frequency of each 4 base genomic sequence appearing in the genomic sequence of ATCGATCG can be obtained. Since frequency of a certain numeric sequence (that is, a specific 4 base sequence) is recorded, for example, in the fifth-digit position of the numeric sequence, each number of frequency can be obtained. In the aforementioned example, after occurrence of the final 4 digit numeric sequence (0, 1, 2, 3) is counted, the resultant record shows "(0, 1, 2, 3, 2)". This means that the number of frequency of sequence (0, 1, 2, 3=ATCG) is 2. In other words, the number of the 5th digit of each numeric sequence obtained after the final numeric sequence is analyzed, may be registered as the total number of frequency.

Figure 6:
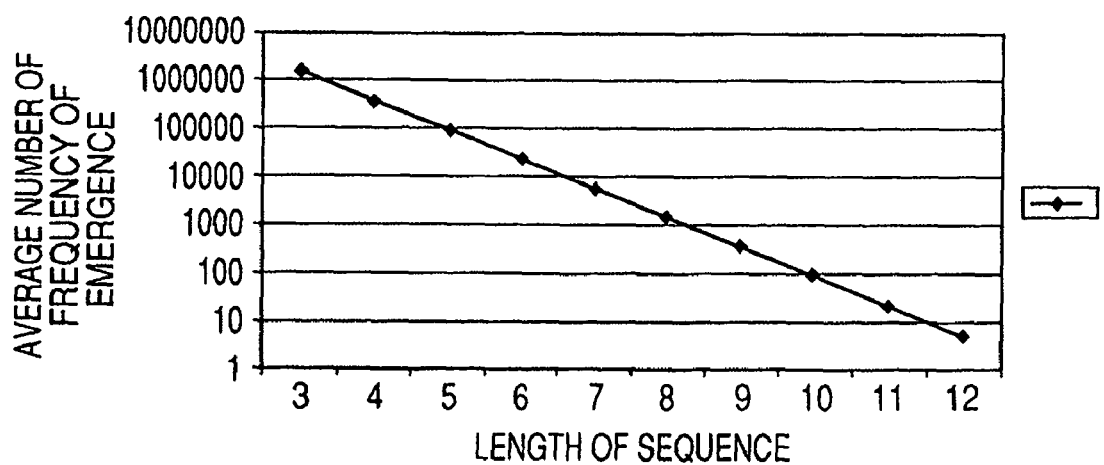
FIG. 6 shows a distribution of numbers of frequency of emergence by sequence length.

The entire genomic sequences registered in the NCBI UniGene sequence database were checked in the same manner, that is number of frequency of each of all possible genomic sequences having 3 to 12 bases estimated from mathematic combinations is summerized. Table 1 shows, for the all genomic sequences registered in the NCBI UniGene sequence database as of July, 2003, the average number of frequency of emergence for each of sequence lengths having 3 to 12 base lengths and the number of sequences of which frequency of emergence is 0. FIG. 6 shows the relationship between the average number of frequency of emergence and the length of a sequence. As is apparent from Table 1, there are sequences of which number of frequency of emergence is 0 when the length of the sequence is 10. Furthermore, as is apparent from FIG. 6 which shows the relationship between the average number of frequency of emergence and the length of a sequence, there is a strong correlation between the sequence length and the number of frequency of emergence. Based on these results, a 9-base sequence of which number of frequency of emergence is low is selected as the original element for constructing a palindromic sequence of control probe to be obtained. Of the $4^9$ sequences which are the possible sequences having 9 bases in the entire genomic sequences registered in the NCBI UniGene sequence database as of July 2003, the sequence of which number of frequency of emergence is lowest was CGTACGATC.

TABLE 1

| Length of sequence (601) | Average number of frequency of emergence (602) | Number of sequences number of frequency of emergence is 0 (603) |
|---|---|---|
| 3 | 1498061 | 0 |
| 4 | 374209 | 0 |
| 5 | 93475 | 0 |
| 6 | 23349 | 0 |
| 7 | 5832 | 0 |
| 8 | 1456 | 0 |
| 9 | 363 | 0 |
| 10 | 90 | 341 |
| 11 | 22 | 86965 |
| 12 | 5 | 2773463 |

Figure 7:
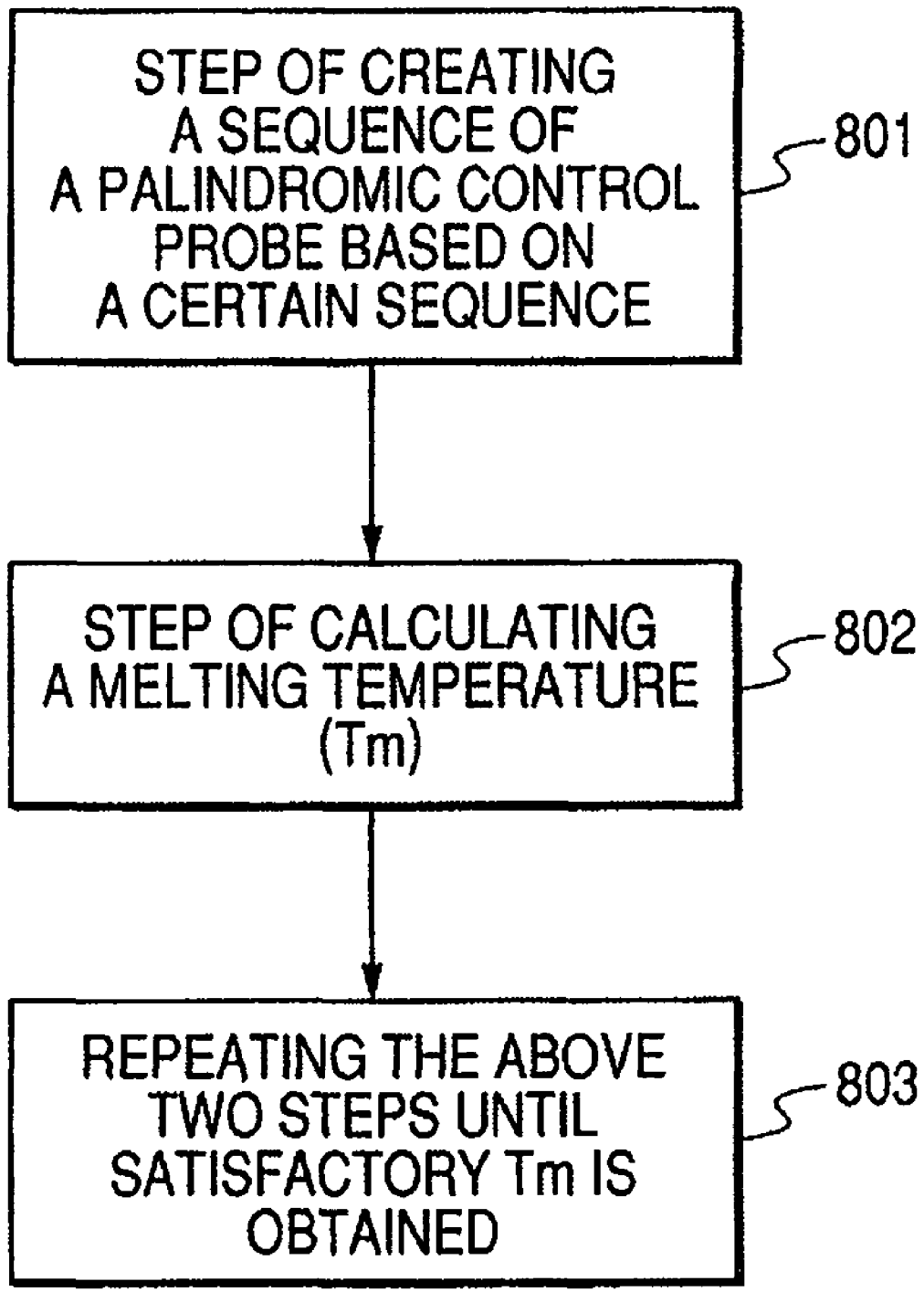
FIG. 7 illustrates a flowchart of designing a control probe sequence satisfying Tm.

Based on the sequence, a control probe with palindromic structure is designed so as to have the length satisfying a requirement, Tm. This time, the required Tm value is now set at 50° C. and the control probe sequence is designed so as to have a palindromic structure. The Tm value is then calculated by the nearest neighbor sequence analysis and whether the designed probe satisfies Tm of 50° C. or not is checked. This procedure is repeated until a palindromic control probe satisfies Tm. The control probe thus obtained is CGTACGATC-GATGTAGCTAGCATGC (SEQ ID No. 1). More specifically, the sequence (SEQ ID No. 1) was determined by setting the base length 9 based on the average number of frequency and arranging aforementioned CGTACGATC of which frequency is low at both terminal sides, and arranging a palindromic structure sequence formed based on GAT, which appears near the tail end portion of the sequence CGTAC-GATC, as the central sequence. FIG. 7 shows a flowchart preferably used in designing a control probe sequence satisfying requisite Tm.

(Design Example and Experimental Example of Control Probe)

Figure 8:
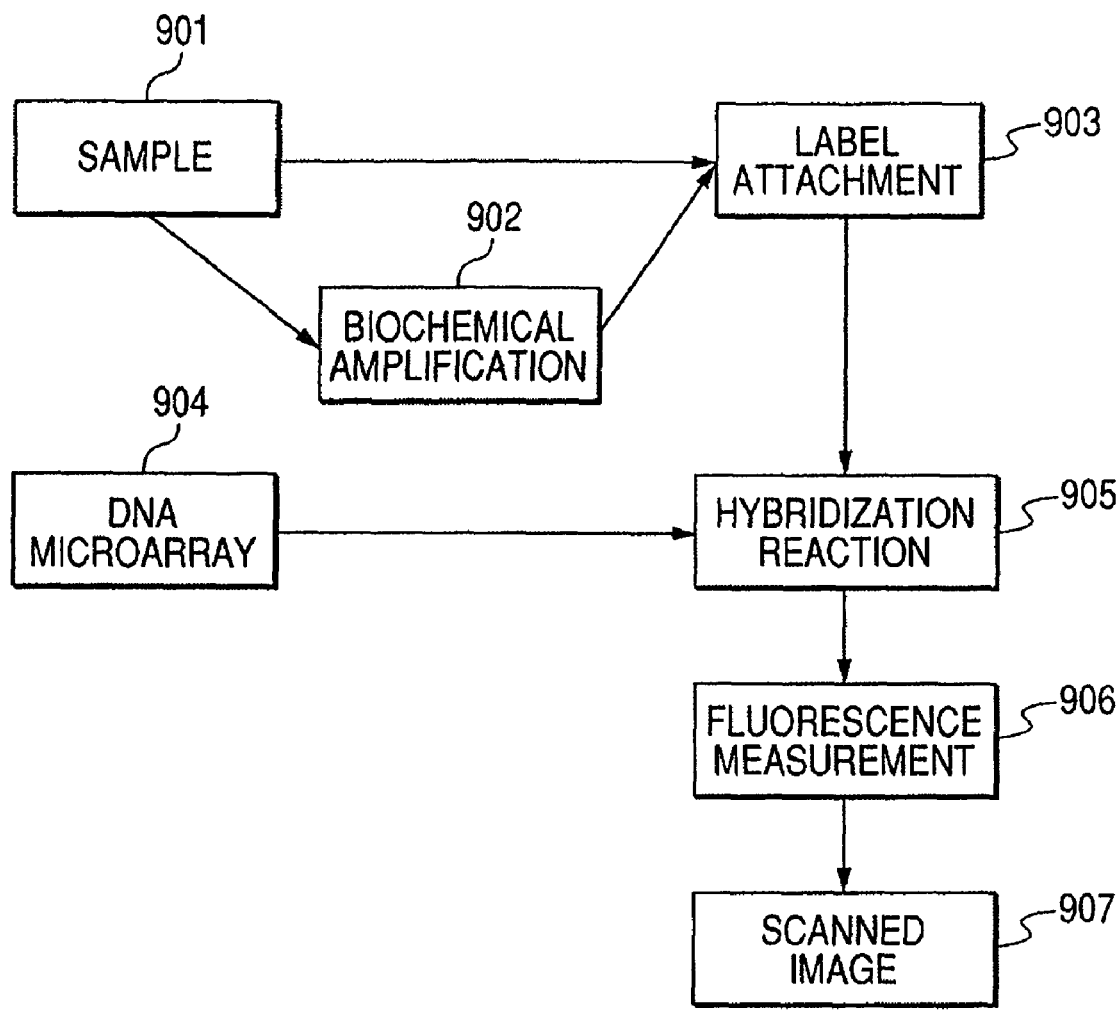
FIG. 8 is an illustration for explaining the procedure for analyzing a nucleic acid by using a probe designed by a designing method for a probe according to an embodiment.

Referring now to FIG. 8, the procedure of an experiment performed by a DNA microarray using a control probe, which is designed by the control probe designing method according to the aforementioned embodiment will be explained. Reference numeral 901 indicates a sample in the form of liquid or solid containing a target nucleic acid. More specifically, when an infectious-disease causal bacterium is specified, use may be made of any specimen possibly containing the bacterium as a sample. Examples of samples include blood derived from a human or an animal such as a livestock; body fluids such as sputum, gastric juice, vaginal secretion and oral mucosa; and excretory substances such as urine and feces. Use may be sometimes made of food possibly causing food poisoning and contaminated with bacteria, a medium possibly contaminated with bacteria including drinking water and environment water such as hot spring water. Furthermore, as a sample, use may be made of an animal and a plant checked in a quarantine station when they are imported or exported.

As a next step 902, the sample 901 is amplified by a "biochemical amplification" method. For example, when an infectious-disease causal bacterium is wished to identify, a target nucleic acid is amplified by the PCR method using a PCR primer designed for detecting 16S rRNA or prepared by further amplifying a PCR amplification product by PCR. Alternatively, a target nucleic acid may be prepared by an amplification method other than PCR, such as the LAMP method.

Thereafter, the sample amplified in the biochemical amplification step 902 or the sample 901 itself is directly labeled with a substance by any one of various labeling methods for visualization (in a labeling step 903). Generally, examples of such a labeling substance include fluorescent substances such as Cy3, Cy5 and rhodamine. Alternatively, a labeling molecule may be sometimes added in the biochemical amplification step 902.

Figure 9:
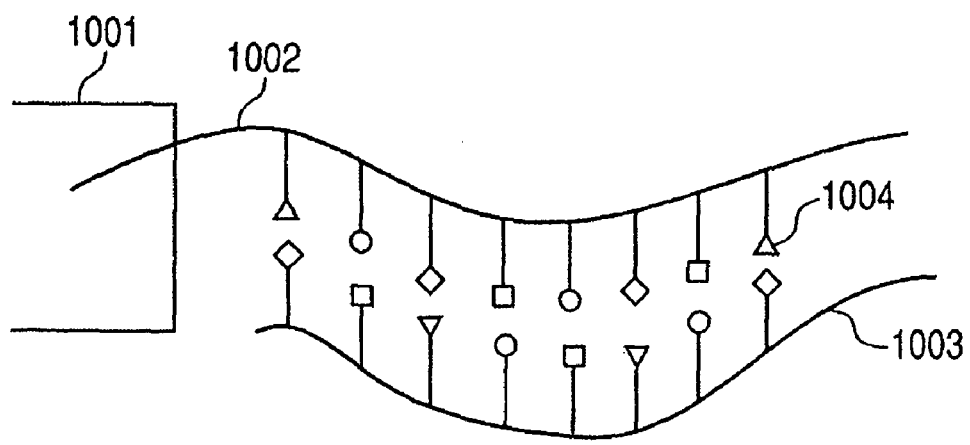
FIG. 9 is an illustration for explaining a hybridization reaction.

The nucleic acid tagged with a labeling molecule is then subjected to a hybridization reaction (905) using a DNA microarray 904, as shown in FIG. 9. For example, when identification of an infectious disease causal bacterium is desired, a probe specific to the bacterium may be immobilized onto a substrate to form the DNA microarray 904. In designing a probe so as to correspond to a bacterium, use may be made of a method by which a sequence specifically identifying the bacterium can be selected from the genomic portion encoding, for example, 16S rRNA. In this method, a complementary sequence to the sequence that is exclusively present in the genomic portion of a target bacterium, while the frequency is 0 in the genomic portion of other bacteria is selected. The DNA microarray 904 has a carrier (substrate) on which a probe(s) are immobilized. As the carrier, use may be made of a planar substrate such as a glass substrate, plastic substrate, or silicon wafer. Alternatively, use may be made of a three-dimensional construct having projections and depressions, beads-like substance, rod-form, string-form, and thread-form substrates. Even if any of them may be used, it does not affect the embodiments and effects of the present invention.

Generally, the surface of a substrate is treated such that a probe DNA can be easily immobilized thereon. In particular, it is preferable to introduce a chemically reactive functional group onto the surface of a substrate. This is because a probe stably binds to the substrate thereby during hybridization resulting in good reproducibility. In the immobilization method employed in this embodiment for example, a combination of a maleimide group and a thiol (—SH) group may be used. To explain more specifically, a thiol (—SH) group is previously bound to an end of a nucleic acid probe, whereas a maleimide group is added to the surface of a solid phase of a substrate. Thereafter, when the nucleic acid probe is supplied to the surface of the solid phase, a thiol group of the nucleic acid probe reacts with a maleimide group in the surface of the solid phase, thereby immobilizing the nucleic acid probe on the substrate surface. A maleimide group is introduced first by reacting an aminosilane coupling agent with a glass substrate, and then applying an EMCS reagent (N-(6-Maleimidocaproyloxy)succinimide, manufactured by Dojindo Laboratories). As a result, an amino group of the aminosilane-coupling agent reacts with the EMCS reagent to introduce a maleimide group into the glass substrate. On the other hand, a thiol (—SH) group is introduced into DNA during synthesis of DNA by a DNA auto-synthesizer by using 5'-Thiol-ModifierC6 (manufactured by Glen Research). Immobilization of probe DNA may be performed by a method using not only the combination of functional groups, but also the combination of an epoxy group (on a solid phase) and an amino group (on nucleic acid probe terminal), for example. As a surface treatment for a substrate, treatment with any silane-coupling agent may be effective. In this case, immobilization is performed by using the functional group introduced by the silane coupling agent and an oligonucleotide having a functional group capable of reacting with the functional group present in the substrate. Furthermore, it is also effective that the surface of a substrate may be coated with a resin having a functional group.

After the hybridization reaction 905, the surface of the DNA microarray 904 is washed to remove nucleic acids unbound to the probes, (generally) dried, and then the fluorescent amount emitted from the hybridized probe 905 is determined (906). The substrate of the DNA microarray 904 is irradiated with excitation light to obtain an image (907) for detecting fluorescent intensity.

The flow of the experiment described In FIG. 8 will be more specifically explained below by taking the case of identifying an infectious disease causal bacterium as a sample. Note that a method of determining biological species according to the present invention may be used in not only identifying an infectious disease causal bacterium as mentioned below but also evaluating human predispositions such as MHC (major histocompatibility antigen complex) as well as analyzing DNA and RNA involved in diseases such as cancer.

(1. Preparation of Probe DNA)

Nucleic acid sequences were designed. The nucleic acid sequence represented by SEQ. ID No. 1 was used as a control probe and the nucleic acid sequences represented by SEQ ID Nos. 2 to 8 shown below were used as probes for detecting *Escherichia Coli*.

```
CTCTTGCCAT CGGATGTGCC CA        (SEQ ID No. 2)

ATACCTTTGC TCATTGACGT TACCCG    (SEQ ID No. 3)

TTTGCTCATT GACGTTACCC GCAG      (SEQ ID No. 4)

ACTGGCAAGC TTGAGTCTCG TAGA      (SEQ ID No. 5)

ATACAAAGAG AAGCGACCTC GCG       (SEQ ID No. 6)

CGGACCTCAT AAAGTGCGTC GTAGT     (SEQ ID No. 7)

GCGGGGAGGA AGGGAGTAAA GTTAAT    (SEQ ID No. 8)
```

The probes for detecting *Escherichia Coli* were formed based on a genomic portion encoding 16S rRNA. After synthesis, to each of the probes shown in SEQ. For ID Nos. 1 to 8, a functional group, that is, a thiol (—SH) group, was introduced into the 5' terminal of the nucleic acid for immobilizing them onto a DNA microarray in accordance with a customary method. After introduction of the functional group, the probes were purified, lyophilized, and stored at −30° C. in a refrigerator.

(2. Preparation of PCR Primer for Amplifying a Specimen)

The nucleic acid sequences shown in Table 2 were designed as PCR primers for amplifying 16S rRNA nucleic acid (target nucleic acid), which were used in detecting a causal bacterium. Specifically, a set of primers for specifically amplifying the genomic portion encoding 16S rRNA were prepared. The primers of the set, which corresponded to both end portions of 16S rRNA coding region of about 1500 bases, were designed such that they had similar specific melting temperatures as much as possible. Note that a plurality of types of primers were designed so as to simultaneously amplify a plurality of 16S rRNA coding regions present in the genome or mutants.

TABLE 2

| | Primer No. | Sequence |
|---|---|---|
| Forward Primer | F-1 | 5' GCGGCGTGCCTAATACATGCAAG 3' (SEQ. ID No. 9) |
| | F-2 | 5' GCGGCAGGCCTAACACATGCAAG 3' (SEQ. ID No. 10) |
| | F-3 | 5' GCGGCAGGCTTAACACATGCAAG 3' (SEQ. ID No. 11) |
| Reverse Primer | R-1 | 5' ATCCAGCCGCACCTTCCGATAC 3' (SEQ. ID No. 12) |
| | R-2 | 5' ATCCAACCGCAGGTTCCCCTAC 3' (SEQ. ID No. 13) |
| | R-3 | 5' ATCCAGCCGCAGGTTCCCCTAC 3' (SEQ. ID No. 14) |

After synthesis, the primers shown in the table were purified by the high performance liquid chromatography (HPLC). Three types of forward primers and three types of reverse primers were mixed and dissolved in a TE buffer such that the final concentration of each primer was 10 pmol/µl.

(3. Extraction of Genomic DNA of *Escherichia coli* (Model Specimen))

(3-1. Culturing Microorganism and Pretreatment for Extracting Genomic DNA)

First, a standard *Escherichia coli* strain was cultured in accordance with a customary method. Then, 1.0 ml of the microbial culture solution (O.D.$_{600}$) was taken and placed in a 1.5 ml of a microtube. Bacterial cells were centrifugally collected at 8500 rpm at 4° C. for 5 minutes. After the supernatant was discarded, 300 µl of enzyme buffer (500 mM Tris-HCl, pH 8.0, 25 mM EDTA) was added to the tube to resuspend the pellet while stirring by a mixer. The bacterial resuspension solution was centrifugally separated at 8500 rpm at 4° C. for 5 minutes to recollect bacterial cells. After the supernatant was discarded, the enzyme solution shown in Table 3 was added to the bacterial cells collected and stirred by a mixer to obtain a resuspension solution.

TABLE 3

| Enzyme | Amount | Concentration |
|---|---|---|
| Lysozyme | 50 µl | (20 mg/ml in Enzyme Buffer) |
| N-Acetylmuramidase SG | 50 µl | (0.2 mg/ml in Enzyme Buffer) |

Then, the bacterial resuspension solution prepared by adding the enzyme solution was allowed to stand still in an incubator at 37° C. for 30 minutes, thereby lysing the bacterial cell wall.

(3-2. Extraction of the Genome)

The genomic DNA of a microorganism was extracted by a nucleic acid purification kit (MagExtractor-Genome-, manufactured by TOYOBO Co., Ltd.) as shown below. To be more specific, first of all, to a pretreated microorganism suspension solution, 750 µl of a dissolution/adsorption solution and 40 µl of magnetic beads were added, and the mixture was vigorously stirred by a tube mixer for 10 minutes (Step 1). Subsequently, the microtube was set on a separation stand (Magical Trapper) and allowed to stand still for 30 seconds. While keeping the magnetic particles gathered on the wall surface of the microtube set on the stand, the supernatant was discarded (Step 2).

Thereafter, 900 µl of washing solution was added to the microtube and the magnetic particles were resuspended by agitating with a mixer for approximately 5 seconds (step 3). Subsequently, the microtube was set on a separation stand (Magical Trapper) and allowed to stand still for 30 seconds. While keeping the magnetic particles gathered on the wall surface of the microtube set on the stand, the supernatant was discarded (Step 4). The steps 3 and 4 were repeated and second washing was performed (Step 5). Thereafter, 900 µl of 70% ethanol was added to the microtube to resuspend the pellet while stirring by a mixer for about 5 seconds (Step 6).

Subsequently, the microtube was set on a separation stand (Magical Trapper) and allowed to stand still for 30 seconds. While keeping the magnetic particles gathered on the wall surface of the microtube set on the stand, the supernatant was discarded (Step 7). The steps 6 and 7 were repeated and second washing was performed with 70% ethanol (Step 8). Thereafter, 100 µl of pure water was added to the resultant magnetic particles and stirred by a tube mixer for 10 minutes.

Subsequently, the microtube was set on a separation stand (Magical Trapper) and allowed to stand still for 30 seconds. While keeping the magnetic particles gathered on the wall surface of the microtube set on the stand, the supernatant was transferred to a new tube to recover it.

(3-3. Evaluation of the Genomic DNA Recovered)

The Genomic DNA of the microorganism (standard *Escherichia coli* strain) thus recovered was subjected to agarose gel electrophoresis and absorbance measurement performed at 260/280 nm in accordance with customary methods. In this manner, the quality (the amount of low molecular nucleic acid contaminants and degree of decomposition) and the amount of the genomic DNA recovered were checked. In this example, about 10 µg of the genomic DNA was recovered. Neither degradation of the genomic DNA nor contamination with rRNA was observed. The Genomic DNA recovered was dissolved in a TE buffer so as to obtain a final concentration of 50 ng/µl and subjected to the following Example.

(4. Preparation of DNA Microarray)

(4-1. Washing of Glass Substrate)

A synthetic quartz glass substrate of 25 mm×75 mm×1 mm (manufactured by Iiyama Tokushu Glass) was placed in a heat- and alkali-resistant rack and soaked in an ultrasonic washing solution having a predetermined concentration previously adjusted. After soaking in the washing solution overnight, ultrasonic washing was performed for 20 minutes. Subsequently, the substrate was taken out, lightly rinsed with pure water, and then, ultrasonic washing was performed for 20 minutes in ultrapure water. Thereafter, the substrate was soaked in a 1N aqueous sodium hydroxide solution heated at 80° C. for 10 minutes. Again, washing with pure water and washing with ultrapure water were performed. In this manner, a quartz glass substrate for a DNA microarray was prepared.

(4-2. Surface Treatment)

A silane coupling agent, KBM-603 (manufactured by Shinetsu Silicone) was dissolved in pure water to a concentration of 1% and stirred at room temperature for 2 hours. Subsequently, the glass substrate previously washed was soaked in the aqueous solution of the silane coupling agent and allowed to stand still at room temperature for 20 minutes. The glass substrate was pulled up, the surfaces of the substrate were lightly washed with pure water, and dried by spraying nitrogen gas onto the both surfaces of the substrate. The substrate thus dried was then baked in an oven heated at 120° C. for one hour to complete the treatment with the coupling agent. In this manner, an amino group was introduced into the surface of the substrate. Subsequently, N-6(-maleimidocaproyloxy) succinimide (hereinafter simply referred to as "EMCS") manufactured by Dojindo Laboratories was dissolved in a solvent mixture containing dimethylsulfoxide and ethanol in a ratio of 1:1 so as to obtain a final concentration of 0.3 mg/ml. In this manner, an EMCS solution was prepared. By this treatment, the amino group introduced by the silane-coupling agent into the surface of the substrate was reacted with the succinimide group of EMCS, with the result that a maleimide group was successfully introduced into the surface of the glass substrate. The glass substrate pulled up from the EMCS solution was washed with the solvent mixture that was used in dissolving EMCS, further washed with ethanol and dried under a nitrogen gas atmosphere.

(4-3. Probe DNA)

The probes prepared in the Section 1 "Preparation of probe DNA" were each dissolved in pure water. Each probe solution was dispensed and lyophilized to remove water so as to be 10 μM as final concentration (a concentration when dissolved in ink).

(4-4. Ejection of DNA by BJ Printer and Binding of DNA Onto a Substrate)

An aqueous solution containing 7.5 wt % of glycerin, 7.5% wt % of thiodiglycol, 7.5 wt % of urea, and 1.0 wt % of acetylenol EH (manufactured by Kawaken Fine Chemical) was prepared. Subsequently, 8 different probes (see the Sequencing List) prepared in Section (1) above were separately dissolved in the solvent mixture mentioned above in a predetermined concentration. Each of the DNA solution thus obtained was loaded into an ink tank of a bubble jet printer (trade name: BJ F-850, manufactured by Canon Corporation) and the ink tank was installed in the print head. The bubble jet printer used herein was modified in structure so as to easily print on a flat board. The bubble jet printer was able to print spots of about 5 pico-liter of a DNA solution at the intervals (pitches) of about 120 micrometers by inputting a printing pattern in accordance with a predetermined file formation method. Subsequently, using the modified bubble jet printer, printing was performed onto a single glass substrate to form an array. Resulting spots were arranged in a matrix pattern of 8 lines×10 rows in such a manner that 10 spots of the same probe were linearly arranged in a line at the intervals of 120 micrometers, and 8 lines of 8 types of probe spots were arranged at the same intervals of 120 micrometers. After it was confirmed that printing was performed without fail, the array was allowed to stand still in a moisture chamber for 30 minutes. In this manner, the maleimide group of the surface of the glass substrate was reacted with the thiol group at the end of a nucleic acid probe.

(4-5. Washing)

After the reaction performed for 30 minutes, the remaining DNA solution on the surface of the substrate was washed away with a 10 mM phosphorous buffer (pH 7.0) containing 100 mM NaCl. As a result a DNA microarray was obtained having single stranded DNA immobilized on the surface of the glass substrate.

(5. Amplification and Labeling of Specimen (PCR Amplification and Fluorescent Label Uptake))

(5-1. Specimen)

The amplification and labeling reaction of a microbial DNA used as a specimen were performed using reagents shown in Table 4 below.

TABLE 4

| Primer PCR reagent (TAKARA ExTaq) | 25 μl | |
| Template Genome DNA | 2 μl | (100 ng) |
| Forward Primer mix | 2 μl | (20 pmol/tube each) |
| Reverse Primer mix | 2 μl | (20 pmol/tube each) |

TABLE 4-continued

| Cy-3 dUTP (1 mM) | 2 μl | (2 nmol/tube) |
| H$_2$O | 17 μl | |
| Total | 50 μl | |

The reaction solution having the composition mentioned above was subjected to an amplification reaction performed in a commercially available thermal cycler in accordance with the following protocol.

TABLE 5

| 95° C. | 10 min. | |
| 92° C. | 45 sec. | |
| 55° C. | 45 sec. | 35 Cycles |
| 72° C. | 45 min. | |
| 72° C. | 10 min. | |

After completion of the reaction, primers were removed by using a purification column (QIAGEN QIAquick PCR Purification Kit), and then, the amount of an amplified product was measured. The amplified product was a labeled specimen.

(5-2. Control Probe)

A fluorescent label was tagged to a target having a complementary sequence of a control probe and used as a control probe target.

(6. Hybridization)

A detection reaction was performed by using the DNA microarray prepared in Section 4 "Preparation of a DNA microarray", the labeled specimen prepared in Section 5 "Amplification and labeling of specimen (PCR amplification and fluorescent label uptake)", and the control probe target.

(6-1. Blocking of DNA Microarray)

BSA (bovine serum albumin, Fraction V, manufactured by Sigma) was dissolved in a 100 nM NaCl/10 mM phosphate buffer to a concentration of 1 wt %. To the solution, the DNA microarray prepared in Section 4 "Preparation of DNA microarray" was soaked at room temperature for 2 hours. In this way, blocking was performed. After completion of blocking, the microarray was washed with a 2×SSC solution (300 mM NaCl, 30 mM sodium citrate (trisodium citrate dihydrate, $C_6H_6Na_3.2H_2O$), pH 7.0) containing 0.1 wt % SDS (dodecyl sodium sulfate), and thereafter, rinsed with pure water, and drained by a spin-dry apparatus.

(6-2. Hybridization)

After drained, the DNA microarray was set at a hybridization apparatus (product name: Hybridization Station manufactured by Genomic Solutions Inc.). A hybridization reaction was performed using the following hybridization solution in the hybridization conditions as shown below.

Hybridization Solution:

6×SSPE/10% formamide/Target (2nd PCR Products, total amount) (6×SSPE: 900 mM NaCl, 60 mM NaH$_2$PO$_4$.H$_2$O, 6 mM EDTA, pH 7.4).

Hybridization Conditions:

After hybridization was performed at 65° C. for 3 minutes, 92° C. for 2 minutes, 45° C. for 3 hours, a microarray was washed with 2×SSC/0.1% SDS at 25° C., with 2×SSC at 20° C., manually rinsed with pure water, and subjected to spin dry.

(7. Detection of Microorganism (Fluorometry))

After completion of the hybridization reaction, fluorescence emitted from a DNA microarray was determined by a fluorometric apparatus for DNA microarray (GenePix 4000B, manufactured by Axon). Whether the hybridization reaction was properly performed or not can be confirmed by checking a brightness of a control probe spot according to the present invention.

Figure 10:
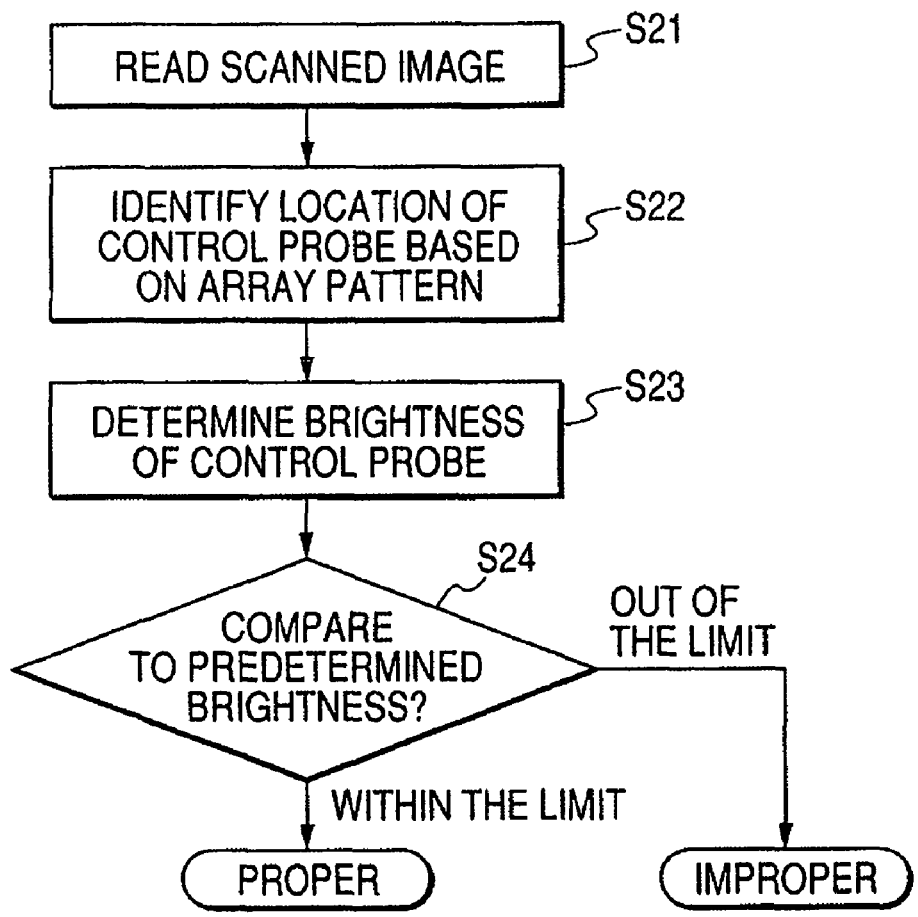
FIG. 10 is a flowchart of judging whether a hybridization reaction is properly performed or not.
Figure 11:
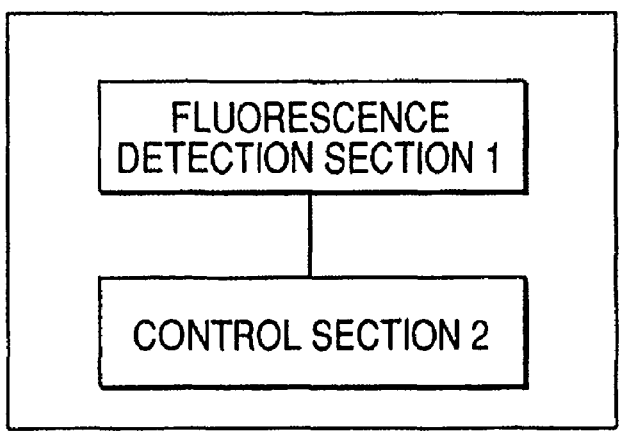
FIG. 11 is a block diagram of a fluorometric apparatus.

A process for checking whether the hybridization reaction was properly performed or not will be illustrated by way of the flowchart shown in FIG. 10. The structure of a fluorometric apparatus is shown in the block diagram of FIG. 11. First, data for detecting fluorescence (secondary scanned image) is read by a control unit 2 (computer) connected to a fluorescence detecting unit 1 of FIG. 11 (S21). Next, the position of a control probe spot in the scanned image thus read is specified based on an array pattern (S22). Subsequently, the brightness of the control probe spot thus specified is measured (S23) and compared to a predetermined brightness (S24). As a result of comparison, if the brightness of the control probe site falls within the predetermined range, it is determined that the hybridization reaction was performed properly. Then, the process goes to an image analysis step. Conversely, if the brightness of the control probe site is outside the predetermined range, it is displayed in a display means or the like that the hybridization reaction failed to perform properly. In this case, the process does not go to the following analysis step. In this manner, the data is subjected to image analysis, only when the hybridization reaction is successfully performed, therefore needless work would not be performed. In addition, it is possible to specify the position of a probe spot to be detected by using the specified position of the control probe spot as a reference. The scanned image analysis can be performed more easily by previously specifying the address of the spot emitting fluorescence.

Furthermore, since the brightness of a plurality of control probe spots showed a nearly constant value, a clear dynamic range was obtained by using an average brightness of the control probe as a maximum brightness (reference brightness).

When a plurality of DNA chips were treated in the same manner and the brightness of control probe spots were checked, they provided a stable value of brightness. As a result, the brightness values of the individual spots can be normalized based on the data of the brightness of a control probe spot. In this case, the brightness of the control probe spot can be used as a reference in mutually comparing a plurality of DNA microarrays, with the result that more accurate detection (e.g., quantitative analysis of a target nucleic acid) can be attained.

As described in the foregoing, according to this embodiment, it is possible to design a control probe suitable for a DNA microarray system. Therefore, the present invention is effective in obtaining more accurate information to identify biological species and individuals.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2005-036545 filed Feb. 14, 2005, which is hereby incorporated by reference herein.

What is claimed is:

1. A control probe, comprising one base sequence heading from the center of the sequence of the control probe toward an end thereof and another base sequence heading from the center toward the other end thereof, wherein both base sequences are part of a base sequence which is identical when read from the 3' side to the 5' side and from the 5' side to the 3' side, and wherein the control probe comprises a base sequence represented by SEQ. ID No. 1.

2. A probe carrier, wherein the probe carrier is a solid phase carrier having a control probe according to claim 1 and a probe for detecting a target sequence contained in a specimen, and wherein both probes are immobilized on the solid phase carrier.

3. A nucleic acid detection kit, comprising the probe carrier according to claim 2 and an artificial nucleic acid having a complementary sequence to that of the control probe.

* * * * *

SEQUENCE LISTING

<160> NUMBER OF SEQ ID NOS: 16

<210> SEQ ID NO 1
<211> LENGTH: 25
<212> TYPE: DNA
<213> ORGANISM: Artificial
<220> FEATURE:
<223> OTHER INFORMATION: Control probe

<400> SEQUENCE: 1
cgtacgatcg atgtagctag catgc                                    25

<210> SEQ ID NO 2
<211> LENGTH: 22
<212> TYPE: DNA
<213> ORGANISM: Artificial
<220> FEATURE:
<223> OTHER INFORMATION: Detecting probe

<400> SEQUENCE: 2
ctcttgccat cggatgtgcc ca                                       22

<210> SEQ ID NO 3
<211> LENGTH: 26
<212> TYPE: DNA
<213> ORGANISM: Artificial
<220> FEATURE:
<223> OTHER INFORMATION: Detecting probe

<400> SEQUENCE: 3
atacctttgc tcattgacgt tacccg                                   26

<210> SEQ ID NO 4
<211> LENGTH: 24

```
<212> TYPE: DNA
<213> ORGANISM: Artificial
<220> FEATURE:
<223> OTHER INFORMATION: Detecting probe

<400> SEQUENCE: 4
tttgctcatt gacgttaccc gcag                                              24

<210> SEQ ID NO 5
<211> LENGTH: 24
<212> TYPE: DNA
<213> ORGANISM: Artificial
<220> FEATURE:
<223> OTHER INFORMATION: Detecting probe

<400> SEQUENCE: 5
actggcaagc ttgagtctcg taga                                              24

<210> SEQ ID NO 6
<211> LENGTH: 23
<212> TYPE: DNA
<213> ORGANISM: Artificial
<220> FEATURE:
<223> OTHER INFORMATION: Detecting probe

<400> SEQUENCE: 6
atacaaagag aagcgacctc gcg                                               23

<210> SEQ ID NO 7
<211> LENGTH: 25
<212> TYPE: DNA
<213> ORGANISM: Artificial
<220> FEATURE:
<223> OTHER INFORMATION: Detecting probe

<400> SEQUENCE: 7
cggacctcat aaagtgcgtc gtagt                                             25

<210> SEQ ID NO 8
<211> LENGTH: 26
<212> TYPE: DNA
<213> ORGANISM: Artificial
<220> FEATURE:
<223> OTHER INFORMATION: Detecting probe

<400> SEQUENCE: 8
gcggggagga agggagtaaa gttaat                                            26

<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9
gcggcgtgcc taatacatgc aag                                               23

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
gcggcaggcc taacacatgc aag                                               23
```

```
<210> SEQ ID NO 11
<211> LENGTH: 23
<212> TYPE: DNA
<213> ORGANISM: Artificial
<220> FEATURE:
<223> OTHER INFORMATION: Primer

<400> SEQUENCE: 11
gcggcaggct taacacatgc aag                                              23

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
atccagccgc accttccgat ac                                               22

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
atccaaccgc aggttcccct ac                                               22

<210> SEQ ID NO 14
<211> LENGTH: 22
<212> TYPE: DNA
<213> ORGANISM: Artificial
<220> FEATURE:
<223> OTHER INFORMATION: Primer

<400> SEQUENCE: 14
atccagccgc aggttcccct ac                                               22

<210> SEQ ID NO 15
<211> LENGTH: 17
<212> TYPE: DNA
<213> ORGANISM: Artificial
<220> FEATURE:
<223> OTHER INFORMATION: Detecting probe

<400> SEQUENCE: 15
atcgatcgac gatcgat                                                     17

<210> SEQ ID NO 16
<211> LENGTH: 17
<212> TYPE: DNA
<213> ORGANISM: Artificial
<220> FEATURE:
<223> OTHER INFORMATION: Detecting probe

<400> SEQUENCE: 16
atcgatcgag ctagcta                                                     17
```